United States Patent [19]
Beck

[11] Patent Number: 5,947,920
[45] Date of Patent: *Sep. 7, 1999

[54] SELF-CONTAINED HYDRATING SYSTEM AND IONTOPHORESIS BIOELECTRODE

[75] Inventor: Jon E. Beck, Salt Lake City, Utah

[73] Assignee: Dermion, Inc., SLC, Utah

[ * ] Notice: This patent issued on a continued prosecution application filed under 37 CFR 1.53(d), and is subject to the twenty year patent term provisions of 35 U.S.C. 154(a)(2).

[21] Appl. No.: 08/821,104

[22] Filed: Mar. 20, 1997

[51] Int. Cl.⁶ ..................................................... A61N 1/30
[52] U.S. Cl. .................. 604/20; 607/153; 220/359.2; 220/523; 222/549.1
[58] Field of Search ............................... 604/20; 607/153; 220/500, 523, 526, 359.1, 359.2, 359.4; 206/557; 222/549.1

[56] References Cited

U.S. PATENT DOCUMENTS

| | | |
|---|---|---|
| 3,946,871 | 3/1976 | Sturm . |
| 5,288,289 | 2/1994 | Haak et al. ................................ 604/20 |
| 5,375,698 | 12/1994 | Ewart et al. . |
| 5,533,972 | 7/1996 | Gyory et al. . |
| 5,582,587 | 12/1996 | Gyory et al. . |
| 5,628,729 | 5/1997 | Okabe . |
| 5,645,527 | 7/1997 | Beck . |
| 5,693,024 | 12/1997 | Flower . |
| 5,713,846 | 2/1998 | Bernhard et al. . |

FOREIGN PATENT DOCUMENTS

WO 93/24177  12/1993  WIPO .

*Primary Examiner*—Mark Bockelman
*Attorney, Agent, or Firm*—Workman, Nydegger & Seeley

[57] ABSTRACT

The present invention provides methods and apparatus permitting at least one hydrating liquid to be maintained in isolation and, when desired, permitting thorough release of the hydrating liquid. In particular, the self-contained hydrating system comprises a releasable seal for isolating hydrating liquid which can be progressively unsealed to release the hydrating liquid. The unsealing process involves an "unpeeling" of the releasable seal and, thus, does not involve breaking or rupturing of the seal material. In this manner, the hydrating liquid is made accessible but is never exposed to broken or ruptured sealing material. The self-contained hydrating system can be manufactured using existing equipment and techniques and can subsequently be easily associated with a separate device requiring hydration when desired.

13 Claims, 4 Drawing Sheets

SELF-CONTAINED HYDRATING SYSTEM AND IONTOPHORESIS BIOELECTRODE

BACKGROUND OF THE INVENTION

1. Technical Field

This invention relates to a self-contained hydrating system for isolating at least one hydrating liquid and for releasing the hydrating liquid when desired. In particular, the invention relates to a self-contained hydrating system usable, for example, to isolate hydrating liquids from an iontophoresis bioelectrode and, when desired, to deliver the hydrating liquids to the iontophoresis bioelectrode.

2. Background Information

Numerous devices require fluid components or fluid communication between components for proper operation. Depending on the type of fluids or for safety, stability or storage purposes, it may be desirable to maintain fluids in a safely isolated but releasable form, e.g., an acid solution for use in a battery. There are also situations where a reaction between a fluid component and another component is important to the operation of a device but it is desirable to control when the reaction occurs. A volatile liquid, such as, for example, a smelling salt solution, may be desired to be maintained in isolation from the environment yet be readily releasable when needed. A self-contained hydrating system for isolating a hydrating liquid and for releasing the hydrating liquid when desired would be useful for purposes such as these.

A particular device requiring hydration for proper operation is an iontophoresis bioelectrode device. Iontophoretic delivery of medicaments is a useful and non-invasive technique having a number of different diagnostic and therapeutic applications. Typically, systems for iontophoretic delivery of medicaments use two conductive elements, one positive and one negative, each placed in electrical contact with a portion of the skin or a mucosal surface of the body. Also typical is that each bioelectrode contains an electrolyte solution at least one of which contains ionized medicament. An electrical power source, such as a battery is connected to the electrodes to complete the electrical circuit through the body. The charge of the ionized solution determines bioelectrode polarity such that, when current is supplied, the medicament ions migrate away from the electrode and are thereby delivered through the skin or mucosal surface of the patient.

Because of storage and solution stability concerns, it is desirable to be able to hydrate the bioelectrode system just prior to use. Some type of enclosure or other fluid-holding means is typically used to contain the ionized electrolyte or medicament solutions and a mechanism or structure on the enclosure is necessary to permit the introduction of solution thereunto. Such structure has typically included some type of orifice containing a plug into which a hypodermic needle or syringe cannula may be inserted to allow delivery of the solution through the orifice into the interior of the enclosure, while preventing the outflow of the solution after it has been introduced into the enclosure. The requirement of such solution receiving mechanism or enclosure increases the cost of the bioelectrode system and gives rise to potential spillage and leakage of solution. Such spillage and leakage can result in an inoperative or defective device.

Bioelectrode systems containing initially dry, but hydratable, solution-holding components and an isolated hydrating liquid which can be released to hydrate the dry components have been developed. See, e.g., Haak et al., U.S. Pat. No. 5,288,289 ("Haak") and Gyory et al., published international patent WO 93/24177 ("Gyory"), the disclosures of which are both incorporated herein by reference. For example, Haak discloses a bioelectrode system comprising breakable capsules filled with the desired hydrating liquid positioned within the material of the hydratable solution-holding components. Squeezing or flexing of the hydrating liquid-storage component breaks the capsules within to release the hydrating liquid. The hydrating liquid flows onto the electrical current distribution element and through preformed passageways to the hydratable solution-holding component. Optional wicking material is described to enhance rapid transfer of the liquid across the electrode conductor surface where the liquid can flow through the passageways to the hydratable solution-holding component.

It can be seen that the hydrating rate, the completeness of the fluid transfer, and the fluid distribution pattern is affected by the characteristics and properties of the separate elements which must be in fluid communication, i.e., the interposed electrical current distribution element material, the hydrating liquid-storage component material, the hydratable solution-holding component material, and the optional wicking material. Other variables include the size, shape, and other characteristics of the flow through openings between the hydrating liquid-storage component and the hydratable solution-holding component, the distributional arrangement of the capsules within the hydrating liquid-storage component material, and even whether or not all of the capsules break or whether the encapsulized liquid is completely dispensed from the broken capsules. Moreover, inadvertent squeezing or flexing of the hydrating liquid-storage component could occur during manufacture, shipping, storing or handling of the device. Such an occurrence could break some or all of the hydrating liquid-filled capsules and cause premature hydration of the hydratable solution-holding component. Such premature hydration could result in an unusable or defective device.

Haak also discloses a bioelectrode system wherein the hydrating liquid-storage component and the hydratable solution-holding component are attached to a first portion of the system while a second portion of the system contains pins for puncturing the hydrating liquid-storage component. In this embodiment, manual alignment and assembly of the first and second portions causes the pins to puncture the hydrating liquid-storage component and thereby release the fluid to hydrate the hydratable solution-holding component. In another embodiment, the system portions are not separate from each other but, rather, are positioned adjacent to each other such that one portion can be folded over to contact the other.

In the above-described devices, the need to manually assemble or manipulate the separate system portions inhibits the occurrence of inadvertent hydration of the hydratable solution-holding component. Nevertheless, separate, or foldable, portions are more costly and cumbersome to use than a unitary device. Such devices also depend on proper assembly by the user and the correct sequence of manipulations of the portions to ensure the hydrating liquid is properly released into the hydratable portion.

Bioelectrode system embodiments disclosed by Gyory include a hydrating liquid-storage component which is separated from a hydratable solution-holding component by a liquid-impermeable sheet. Certain embodiments rely on packaging means to protect from inadvertent release of the hydrating liquid and to cause "automatic" hydration upon removal of the device from the package. The packaging means which effect "automatic" hydration include compression means to rupture or burst the liquid-impermeable sheet;

a blade to puncture the liquid-impermeable sheet; and a pull-tab to rip or tear the liquid-impermeable sheet. An alternative embodiment attaches the pull-tab for ripping or tearing the liquid impermeable sheet to a release liner covering a skin contacting surface of the device. In this embodiment, removal of the release liner prior to placement on the patient "automatically" pulls the pull-tab means to rip or tear the liquid-impermeable sheet and thereby release the hydrating liquid. Like Haak, Gyory also discloses liquid flow control means for directing the flow of hydrating liquid through the breached liquid-impermeable sheet to the hydratable solution-holding component.

It can be seen that, in Gyory's devices, it is the liquid-impermeable sheet separating the hydrating liquid-storage component from the hydratable solution-holding component which is physically ruptured, punctured, or ripped. The material comprising the hydrating liquid-storage component, however, remains intact. After the liquid-impermeable sheet is breached and the hydrating liquid is released, the material which formed the now-depleted hydrating liquid-storage component remains positioned within the device. In the case of a ruptured or punctured sheet, all of the now-breached liquid-impermeable sheet material also remains entirely within the device. In the pull-tab embodiment, some of the sheet material is ripped or torn away and is removed from within the device with the attached pull-tab. Nevertheless, in all cases, a substantial portion of the liquid-impermeable sheet material as well as the material comprising the depleted hydrating liquid-storage component remains within the device following the hydration process.

The rupturing, puncturing, or tearing of the liquid-impermeable sheet material exposes torn edges and, thus, inner layers, of the liquid-impermeable sheet including, for example, foil edges. The hydrating liquid-storage component material and the breached liquid-impermeable sheet material, including exposed torn inner layer edges, remain within the device. These no-longer needed materials could interfere with electrical current distribution. These materials also maintain fluid communication with the now-hydrated solution-holding component such that deleterious interaction with the solution is possible. For example, over long-term iontophoresis, i.e. many hours, materials such as exposed foil edges could corrode. Both Haak and Gyory provide liquid-conveying pathways to distribute the hydrating liquid. Such liquid-conveying pathways, however, necessarily affect the transfer of the hydrating fluid because the rate and amount of fluid transferred is limited by the pathway configuration.

It would be an advancement to provide methods and apparatus for isolating a hydrating liquid and for rapidly and thoroughly releasing the hydrating liquid when desired. It would be advantageous to provide such methods and apparatus which are simple and reliable. It would be a further advantage to provide such methods and apparatus which are self-contained and can be produced in a cost-effective and efficient manner and which can easily be subsequently associated with an apparatus to be hydrated when desired.

SUMMARY OF THE INVENTION

It is a primary object of the present invention to provide a self-contained hydrating system for isolating at least one hydrating liquid and, when desired, for rapidly and efficiently releasing the hydrating liquid.

Another object of the present invention is to provide a self-contained hydrating system for evenly distributing the hydrating liquid onto the associated hydratable matrix element.

It is another object of the present invention to provide a self-contained hydrating system which does not require cumbersome or precise assembly, alignment, or other manipulations to effect release of the hydrating liquid.

A further object of the present invention is to provide a self-contained hydrating system which permits the isolated hydrating liquid to be made substantially entirely available.

A further object of the present invention is to provide a self-contained hydrating system which is simple to manufacture and simple to operate.

Yet another object of the present invention is to provide a self-contained hydrating system which can be used to isolate more than one hydrating liquid and to release the multiple hydrating liquids either sequentially or simultaneously.

An additional object of the present invention is to provide a self-contained hydrating system which can be manufactured using existing equipment and techniques and commercially available, standard materials and which can subsequently be easily associated with a separate device requiring hydration when desired.

These and other objects and advantages of the invention will be better understood by reference to the detailed description, or will be appreciated by the practice of the invention.

To achieve the foregoing objects, and in accordance with the invention as embodied and broadly described herein, the apparatus of the invention comprises a self-contained hydrating system for isolating at least one hydrating liquid and, when desired, for simply and thoroughly releasing the hydrating liquid. In particular, the self-contained hydrating system comprises a releasable seal for a hydrating liquid storage cavity formed in a tray which can be progressively unsealed to release the hydrating liquid. The unsealing process involves an "unpeeling" of the releasable seal and, thus, does not involve breaking or rupturing of the seal material. In this manner, the hydrating liquid is made accessible but is never exposed to broken or ruptured sealing material. An exemplary use of the self-contained hydrating system is to provide hydration for a hydratable iontophoresis bioelectrode system.

BRIEF DESCRIPTION OF THE DRAWINGS

In order that the manner in which the above-recited and other advantages and objects of the invention are obtained may be understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention provides methods and apparatus permitting at least one hydrating liquid to be maintained in isolation and, when desired, permitting thorough release of the hydrating liquid. The self-contained hydrating system is simple to operate and does not require cumbersome or precise assembly, alignment, or other manipulations to effect controlled release of the hydrating liquid. The self-contained hydrating system can be used to isolate more than one hydrating liquid and to release the multiple hydrating liquids either sequentially or simultaneously.

In particular, the self-contained hydrating system comprises a releasable seal for isolating hydrating liquid which can be progressively unsealed to release the hydrating liquid. The unsealing process involves an "unpeeling" of the releasable seal and, thus, does not involve breaking or rupturing of the seal material. In this manner, the hydrating liquid is made accessible but is never exposed to broken or ruptured sealing material. The self-contained hydrating system can be manufactured using existing equipment and techniques and commercially available, standard materials and can subsequently be easily associated with a separate device requiring hydration when desired.

Figure 1:
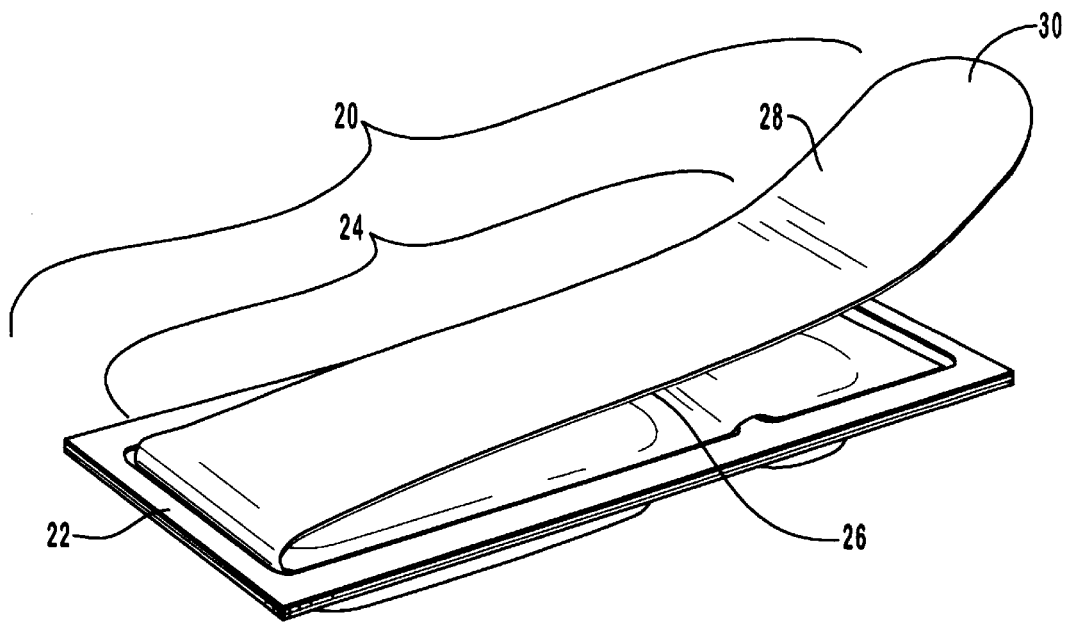
FIG. 1 is a perspective top view of a preferred embodiment of the self-contained hydrating system of the present invention.
Figure 2:
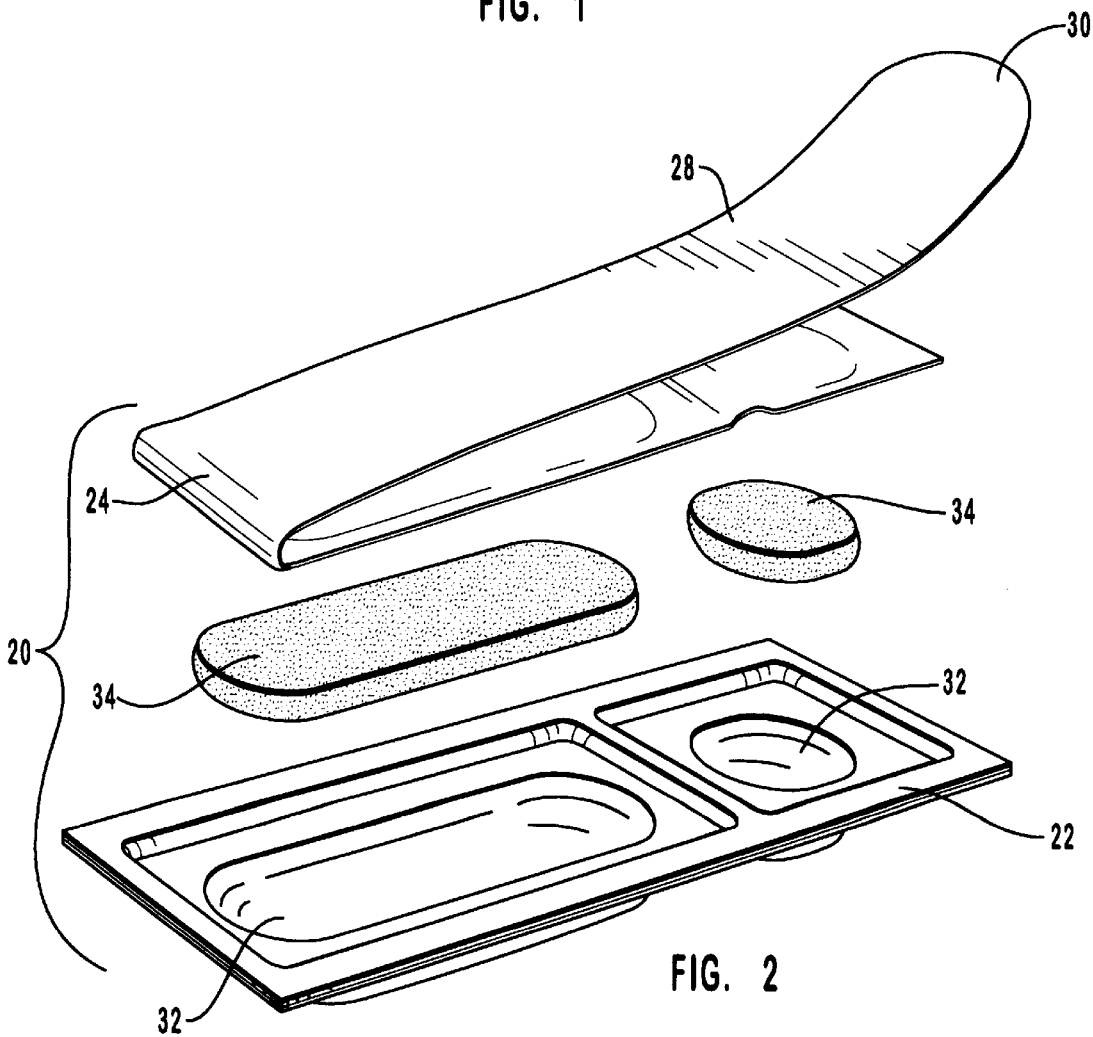
FIG. 2 is an exploded view of components of the preferred embodiment of the self-contained hydrating system shown in FIG. 1.

In the accompanying drawings, FIG. 1 illustrates a presently preferred self-contained hydrating system 20 constructed in accordance with the present invention. The self-contained hydrating system of the present invention is preferably a compact, lightweight, and largely disposable integral unit. The self-contained hydrating system comprises a tray element 22 adapted to contain at least one hydrating liquid (not visible in FIG. 1). A releasable seal element 24 isolates the hydrating liquid contained within the tray element 22. The releasable seal element 24 preferably comprises a strip of suitable material folded upon itself such that a bottom portion 26 is releasably sealed to the tray element 22 to thereby isolate the hydrating liquid contained therein and a top portion 28 is folded back upon, and aligned with, the underlying bottom portion 26. For illustration purposes, top portion 28 is shown lifted up from the underlying bottom portion 26. When the hydrating system is associated with a separate device requiring hydration, however, the top portion 28 will usually be in contact with the bottom portion 26 as shown in FIG. 2. The top portion 28 of the strip has a tab member 30 formed at the end opposite the end that is folded to form the bottom portion 26. FIG. 2 illustrates an exploded view of the components of the preferred embodiment of FIG. 1. As seen in FIG. 2, tray element 22 is formed with cavities 32 to contain the hydrating liquids 34. Once the desired quantity of the selected hydrating liquids is positioned within the cavities, the bottom portion 26 of the releasable seal element 24 is releasably sealed to the tray around each cavity to thereby isolate the hydrating liquids therein. To ensure that the hydrating liquids are isolated from each other, the cavities are preferably separated from each other by a divider portion of tray element 22. As seen in FIGS. 1 and 2, the tray element 22 preferably is formed with slight depressions surrounding the underlying cavities 32 and which correspond to the size and shape of the bottom portion 26 of the strip. The depressions permit the bottom portion 26 of the strip to be sealed more securely around the cavities 32. The top portion 28 of the strip is freely movable and has a tab member 30 formed at the end where the top portion 28 extends beyond the underlying bottom portion 26.

At least the bottom portion of the releasable seal element comprises a liquid-impermeable material and has a surface capable of being releasably sealed to the tray element by a suitable releasable sealing method such as heat sealing, crimping, or a pressure sensitive adhesive. For example, a suitable material would be a high moisture barrier, heat seal peelable, puncture-resistant packaging material such as TPC-0760 manufactured by Tolas Health Care Packaging, Feasterville, Pa. TPC-0760 comprises polyester film, LD polyethylene, foil, ionomer, and a heat seal coating. It will be appreciated that the same material may be used for the entire releasable seal element or another material may be used for the top portion and the tab element, if desired.

Figure 3:
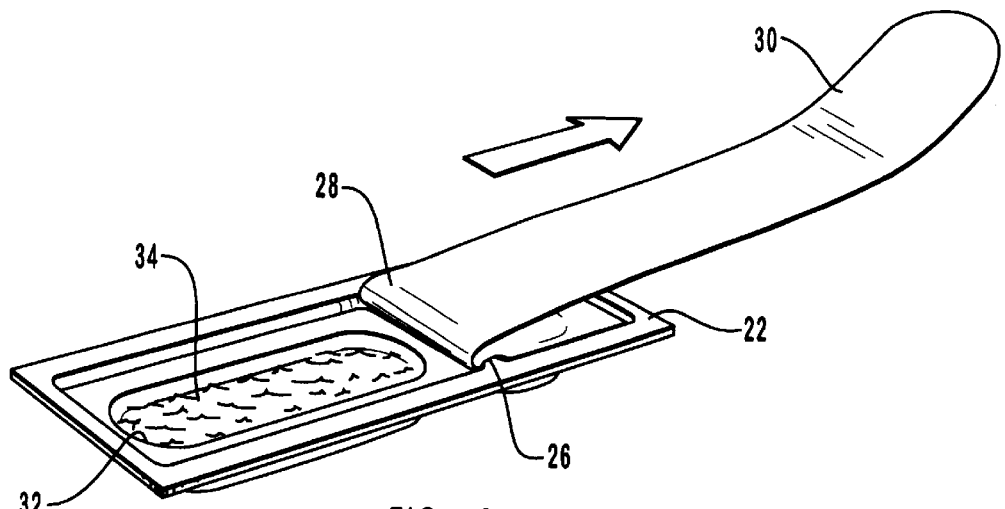
FIG. 3 is a perspective view of the preferred embodiment of FIG. 1 during a first stage of releasing the hydrating liquid.
Figure 4:
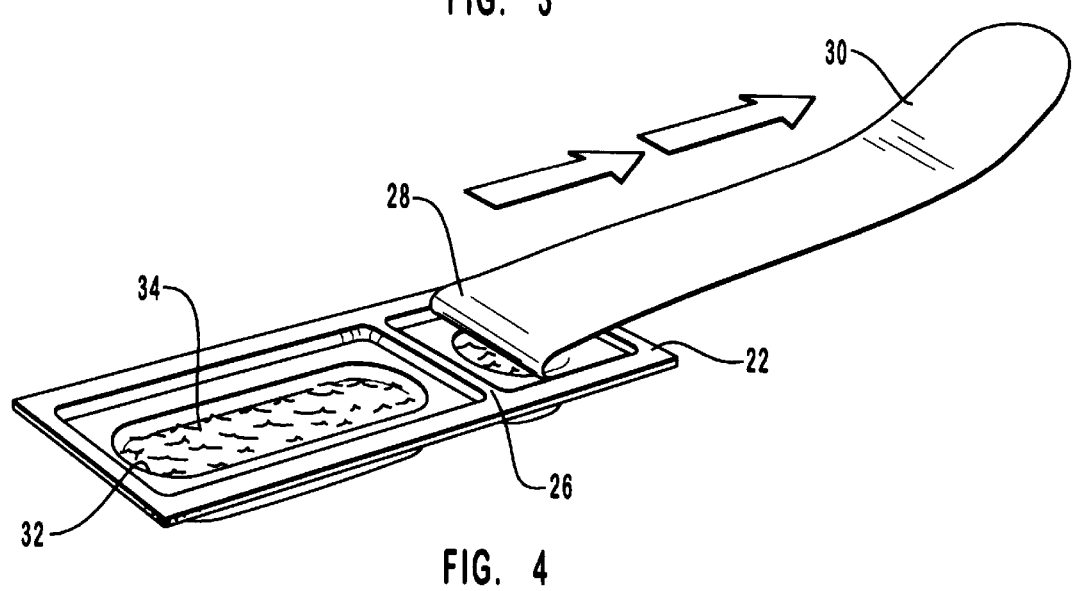
FIG. 4 is a perspective view of the preferred embodiment of FIG. 1 during a second stage of releasing the hydrating liquid.
Figure 5:
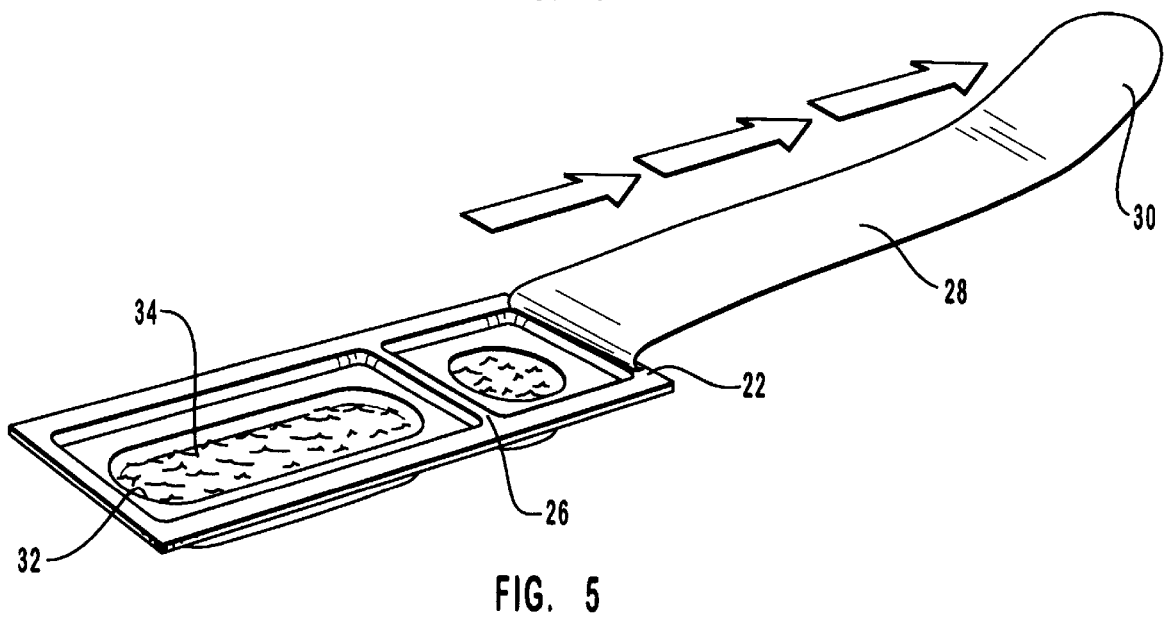
FIG. 5 is a perspective view of the preferred embodiment of FIG. 1 during a third stage of releasing the hydrating liquid.

The isolated hydrating liquids 34 within the cavities 32 formed in the tray element 22 are made accessible by operation of the tab member 30. Various stages of the unsealing process are illustrated in FIGS. 3–5. It can be seen that pulling the tab member 30 such that the top portion 28, while remaining aligned with the bottom portion, is moved away from the underlying bottom portion 26 results in progressive inversion of the bottom portion upon itself and, simultaneously, progressive unsealing from the tray element 22. Continued pulling of tab member 30 will result in complete unsealing and separation of the releasable seal element 24 from the tray element 22. Unsealing of the releasable seal element 24 permits access to the hydrating liquids 34 contained in tray element 22.

Although two cavities and two hydrating liquids are shown in FIG. 2, it will be appreciated that the number may be varied to suit the specific purpose. Thus, one or more hydrating liquids may be contained within corresponding cavities formed in the tray element.

It will be further appreciated that multiple cavities may be configured such that a single releasable seal element can isolate all of the hydrating liquids as shown in FIG. 2. Alternatively, multiple releasable seal elements could be used to separately isolate multiple hydrating liquids.

Figure 6:
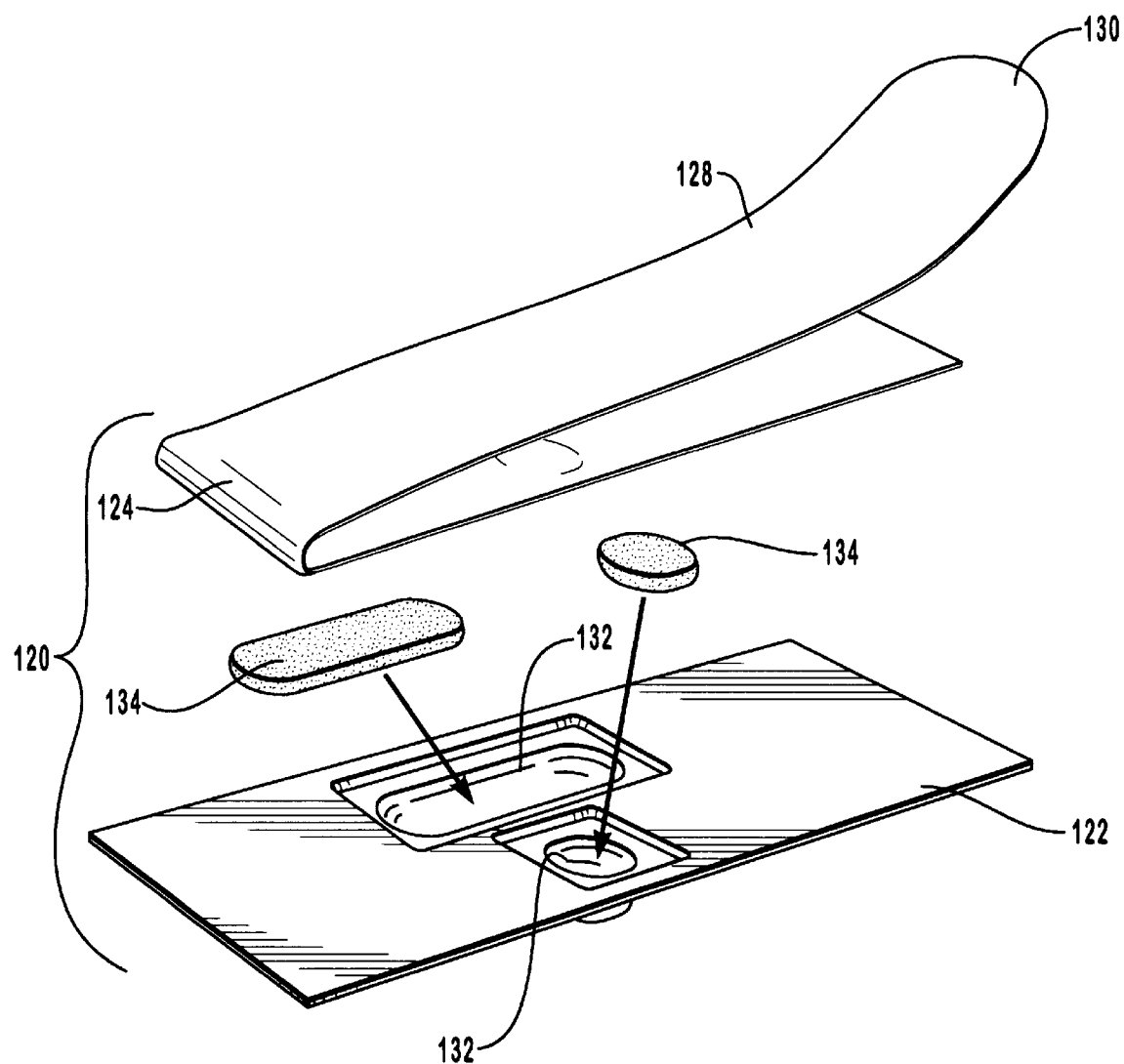
FIG. 6 is an exploded view of components of another preferred embodiment of the self-contained hydrating system of the present invention.

Moreover, release of multiple hydrating liquids can occur sequentially or simultaneously depending on the configuration of cavities and seal elements and/or on the selected sequence of performing, and completing, the unsealing operations. FIG. 6 illustrates an exploded view of an alternative embodiment of the self-contained hydrating system of the present invention wherein two cavities for containing hydrating liquids are configured for simultaneous unsealing. As shown, tray element 122 is formed with cavities 132 to contain the hydrating liquids 134. Once the desired quantity of the selected hydrating liquids is positioned within the cavities, the bottom portion 126 of the releasable seal element 124 is releasably sealed to the tray around each cavity to thereby isolate the hydrating liquids therein. As described previously, the isolated hydrating liquids 134 within the cavities 132 formed in the tray element 122 are simultaneously made accessible by operation of the tab member 130. Pulling the tab member 130 such that the top portion 128, while remaining aligned with the bottom portion, is moved away from the underlying bottom portion 126 will result in progressive inversion of the bottom portion upon itself and, simultaneously, progressive unsealing from the tray element 122. Continued pulling of tab member 130 will result in complete unsealing and separation of the releasable seal element 124 from the tray element 122.

One exemplary use of the self-contained hydrating system of the present invention is to isolate hydrating liquids from a matrix element of an iontophoresis bioelectrode and, when desired, to deliver the hydrating liquids to the matrix element of the iontophoresis bioelectrode. References to such a matrix element will hereinafter be referred to as "hydratable" when used to indicate the initial "dry," i.e., non-hydrated, state and as "hydrated" to indicate the state following hydration. The self-contained hydrating system of the present invention permits the isolated hydrating liquid to be made substantially entirely available upon release. Thus, in association with hydratable matrix elements contained within an iontophoretic bioelectrode, for example, substantially all of the hydrating liquid is available for transfer to the hydratable matrix elements to thereby ensure accurate achievement of desired ion concentrations and proper saturation of the hydratable matrix elements thus increasing the accuracy of calculated iontophoretically delivered medicament dosage.

Iontophoretic delivery of medicaments is a useful and non-invasive technique having a number of different diagnostic and therapeutic applications. Typically, systems for iontophoretic delivery of medicaments use two bioelectrodes, one positive and one negative, each placed in electrical contact with a portion of the skin or a mucosal surface of the body. An electrical power source, such as a battery, is connected to the electrodes, to complete the electrical circuit through the body. Also typical is that each bioelectrode contains an electrolyte solution at least one of which contains ionized medicament. The electrolyte solutions are placed in fluid communication with the skin or mucosal surface The charge of the ionized solution determines bioelectrode polarity such that, when current is supplied, the medicament ions migrate away from the electrode and are thereby delivered through the skin or mucosal surface of the patient.

An exemplary bioelectrode system for use with the self-contained hydrating system of the present invention is adapted to be manufactured and stored in an initially "dry" state to avoid problems associated with the manufacture, storage, handling, stability, and use of pre-hydrated bioelectrodes. Typically, a first hydratable matrix element is intended to contain ionized medicament solution. A second hydratable matrix element is generally intended to contain a dispersive electrolyte solution. Initially, the matrix elements are "dry" but "hydratable" because they must be hydrated with a suitable liquid prior to use. The dry matrix elements may contain a dry form of the desired medicament or electrolyte solution which is hydrated with an appropriate diluent or the dry matrices may contain only support material which is hydrated with the appropriate medicament or electrolyte solution. It may also be possible to store and handle combinations of medicaments wherein some are stable in dry form and some are stable in hydrated form but the combination is not stable and must be kept separated prior to use. The stable dry medicaments can be stored in the dry matrix element and the medicaments which are stable in hydrated form can be supplied with the hydrating liquid.

A presently preferred bioelectrode system comprises an integral unit assembled from various components, such as hydratable matrix elements for containing the electrolyte and/or medicament solutions, current distribution elements formed on a suitable substrate, and a power source. The present invention provides a self-contained hydrating system which can be manufactured separately and then easily associated with a bioelectrode system having hydratable matrix elements. For example, the self-contained hydrating system of the present invention can be manufactured to isolate the desired quantities of selected hydrating fluids in the suitable configuration for aligning with the hydratable matrix elements of a separately manufactured and assembled bioelectrode system or portion thereof.

Figure 7:
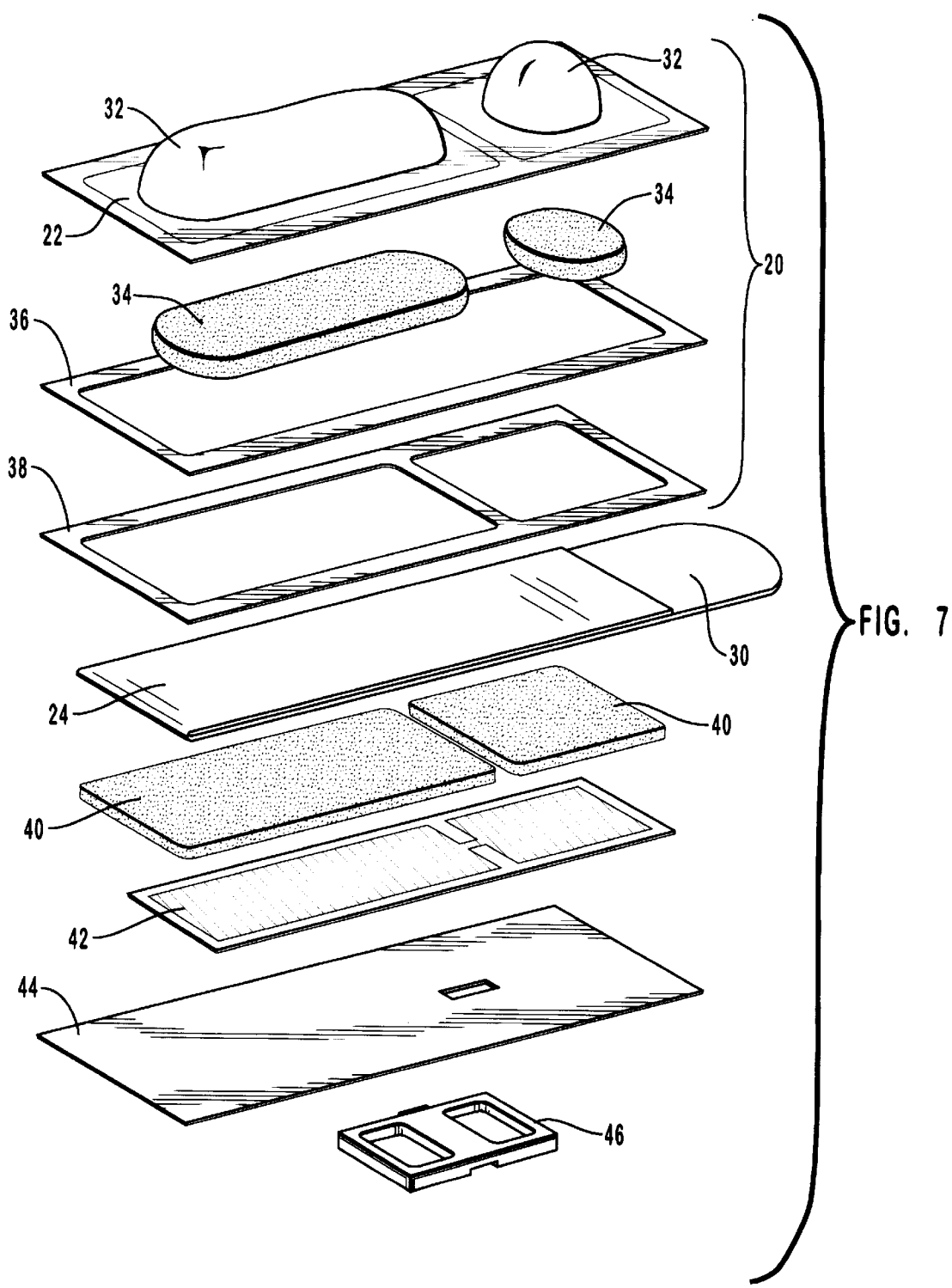
FIG. 7 is an exploded view of some components of a bioelectrode system adapted to be removably attached to another preferred embodiment of the self-contained hydrating system of the present invention.

FIG. 7 illustrates an exploded view of some components of a bioelectrode system adapted to be removably attached to a preferred embodiment of the self-contained hydrating system 20 of the present invention. The self-contained hydrating system 20 is removably affixed in a known manner, for example, with an adhesive layer 36 and release layer 38, to the skin fixation element 44 of the bioelectrode system. As shown, release layer 38 preferably is configured with openings which correspond to the separate cavities and divider portion of the mounting tray to provide an additional layer of separation between the cavities.

As shown in FIG. 7, a preferred embodiment of the self-contained hydrating system 20 comprises means to effect attachment to a separate device requiring hydration. For example, the tray element 22 preferably has a release layer 36 attached with an adhesive layer 38 to the surface of the tray element which will face the hydration-requiring component of the separate device. The release layer permits the self-contained hydrating system 20 to be attached and detached from the separate device, if desired. The release layer preferably is configured to correspond to the cavities and the divider configured in the tray element. In this manner, the release layer also helps ensure that the hydrating liquids remain isolated from each other.

The skin fixation element 44 has a suitable adhesive on the skin surface facing side. For ease of use, a corner of the skin fixation element can be adhesive-free to permit the user to begin the separation from the release layer at that point. Alternatively, the skin fixation element may comprise an extending tab member for grasping while effecting separation from the release layer. Also affixed to the skin fixation element are the current distribution element 42 and the hydratable matrix elements 40. When assembled, the hydratable matrix elements 40 are aligned with and adjacent to the top portion 28 of the releasable seal element 24 and, thus, also aligned with the underlying cavities 32 containing the hydrating liquids 34. An attachment 46 for a power source is positioned on the outward-facing surface of the skin fixation element 44.

When assembled as shown in FIG. 7, the self-contained hydrating system 20 is reversibly affixed to the skin or mucosal surface-facing side of the bioelectrode system such that operation of the tab member 30 results in the hydrating liquids 34 becoming accessible to the adjacent hydratable matrix elements 40. Preferably, the entire assembly of bioelectrode system and removably affixed self-contained hydrating system is positioned on a table or other stable surface with the cavities containing the hydrating liquid facing upward and the tab member extending from a side. The assembly is held steady while the tab member is operated, i.e., pulled away from the assembly while keeping the top portion of the releasable seal element generally aligned with the bottom portion. As the cavities become unsealed, gravity will cause the hydrating liquid to contact the hydratable matrix elements. In this manner, the hydratable matrix elements are rapidly, evenly, and thoroughly hydrated.

It will be appreciated that the tab member may be operated from any position and that the entire assembly can then be easily turned to cause the hydrating liquid to flow onto the adjacent matrix elements. When the hydrating liquid is completely dispensed, the self-contained hydrating system, minus the hydrating liquid, can be disassociated from the now-hydrated and ready to use bioelectrode system by, for example, peeling the release liner away from the skin fixation element.

The present invention may be embodied or utilized in other specific forms or manners without departing from its spirit or essential characteristics. The described embodiments and methods are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A self-contained hydrating system comprising:
    a tray element;
    a cavity formed within said tray element to receive a hydrating liquid;
    a hydrating liquid placed within said cavity;
    a depression formed within said tray element around the periphery of said cavity, said depression configured to aid in isolating said hydrating liquid within said cavity; and
    a releasable seal element having a bottom portion releasably sealed to said depression to thereby isolate said hydrating liquid within said cavity and a top portion folded over and aligned with said bottom portion, said top portion extending beyond said bottom portion and terminating in a tab member;
    wherein operation of said tab member cause progressive unscaling of the bottom portion of said releasable seal element from said tray element to thereby expose said cavity and said hydrating liquid.

2. A self-contained hydrating system as defined in claim 1 wherein said bottom portion is releasably sealed to said tray element by heat welding.

3. A self-contained hydrating system as defined in claim 1 wherein said bottom portion is releasably sealed to said tray element with pressure sensitive adhesive.

4. A self-contained hydrating system as defined in claim 1 further comprising means for releasably attaching to a device requiring hydration.

5. A self-contained hydrating system as defined in claim 1, wherein said tray element is further provided with a divider portion, said divider portion configured to assist said depression and said releasable seal element to isolate said hydrating liquid within said cavity.

6. A self-contained hydrating system as defined in claim 1, wherein said tray element is provided with two cavities, said tray element being further configured with a divider portion between said two cavities such that said divider portion assist said depression and said releasable seal element to isolate said hydrating liquid within said two cavities.

7. A hydratable bioelectrode element for use in an iontophoretic delivery device comprising:
    an electrical current distribution element;
    a hydratable matrix member in electrical communication with the electrical current distribution element;
    hydration means positioned to fluidly communicate with the hydratable matrix member for hydrating said matrix member, said hydration means including a self-contained hydrating system comprising:
    a tray element;
    a cavity formed within said tray element to receive a hydrating liquid;
    a hydrating liquid placed within said cavity;
    a depression formed within said tray element around the periphery of said cavity, said depression configured to aid in isolating said hydrating liquid within said cavity; and
    a releasable seal element having a bottom portion releasably sealed to said depression to thereby isolate said hydrating liquid within said cavity and a top portion folded over and aligned with said bottom portion, said top portion extending beyond said bottom portion and terminating in a tab member;
    wherein operation of said tab member causes progressive unsealing of the bottom portion of said releasable seal element from said tray element to thereby expose said cavity and said hydrating liquid.

8. A self-contained hydrating system comprising:
    a tray element;
    a plurality of cavities formed within said tray element;
    a hydrating liquid placed within said plurality of cavities;
    a divider portion located between said plurality of cavities, said divider assisting in isolating said hydrating liquid within said plurality of cavities; and
    a releasable seal element having a bottom portion releasably sealed to said tray element and said divider portion to thereby isolate said hydrating liquid within said plurality of cavities and a top portion folded over and aligned with said bottom portion, said top portion extending beyond said bottom portion and terminating in a tab member;
    wherein operation of said tab member causes progressive unsealing of the bottom portion of said releasable seal element from said tray element to thereby expose said plurality of cavities and said hydrating liquid.

9. A self-contained hydrating system as defined in claim 8 wherein said tray element is further configured with a depression formed around the periphery of said plurality of cavities, said depression configured to assist said depression and said releasable seal element to isolate said hydrating liquid within said plurality of cavities.

10. A self-contained hydrating system as defined in claim 9 wherein said bottom portion is releasably sealed to said tray element by heat welding.

11. A self-contained hydrating system as defined in claim 9 wherein said bottom portion is releasably sealed to said tray element with pressure sensitive adhesive.

12. A self-contained hydrating system as defined in claim 8 further comprising means for releasably attaching to a device requiring hydration.

13. A self contained hydrating system comprising:
    a tray element;
    a plurality of cavities formed within said tray element to receive a hydrating liquid;
    a hydrating liquid placed within said plurality or cavities;
    a depression formed within said tray element around the periphery of said plurality of cavities, said depression configured to aid in isolating said hydrating liquid within said cavity;
    a divider portion located between said plurality of cavities, said divider portion configured to assist said depression to isolate said hydrating liquid within said plurality of cavities.

a releasable seal element having a bottom portion releasably sealed to said depression and said divider portion to thereby isolate said hydrating liquid within said plurality of cavities and a top portion folded over and aligned with said bottom portion, said top portion extending beyond said bottom portion and terminating in a tab member;

wherein operation of said tab member causes progressive unsealing of the bottom portion of said releasable seal element from said tray element to thereby expose said plurality of cavities and said hydrating liquid.

* * * * *

UNITED STATES PATENT AND TRADEMARK OFFICE
CERTIFICATE OF CORRECTION

PATENT NO. : 5,947,920

DATED : September 7, 1999

INVENTOR(S) : Jon E. Beck

It is certified that error appears in the above-identified patent and that said Letters Patent is hereby corrected as shown below:

Col. 10, line 59                                             After the word "plurality" delete "or" and insert instead -- of --.

Signed and Sealed this

Ninth Day of January, 2001

Attest:

Q. TODD DICKINSON

*Attesting Officer*              *Commissioner of Patents and Trademarks*